United States Patent [19]

Berch et al.

[11] Patent Number: 4,820,280

[45] Date of Patent: Apr. 11, 1989

[54] PASS-THROUGH TUBE FOR PRESURIZED CHAMBER

[75] Inventors: Stephen W. Berch, Arvada; Leslie M. Baines, Boulder, both of Colo.

[73] Assignee: Cobe Laboratories, Inc., Lakewood, Colo.

[21] Appl. No.: 6,366

[22] Filed: Jan. 23, 1987

[51] Int. Cl.[4] .......... A61M 5/005

[52] U.S. Cl. .......... 604/248; 604/283; 604/905

[58] Field of Search .......... 604/246, 248, 283, 905

[56] References Cited

U.S. PATENT DOCUMENTS

| | | | |
|---|---|---|---|
| 2,854,027 | 9/1958 | Kaiser et al. | 604/248 |
| 3,276,472 | 10/1966 | Jinkens et al. | 604/248 |
| 4,346,703 | 8/1982 | Dennehey et al. | 604/905 |
| 4,369,781 | 1/1983 | Gilson et al. | 604/905 |
| 4,452,473 | 6/1984 | Ruschke | 604/905 |
| 4,485,014 | 11/1984 | Gilroy et al. | 604/283 |
| 4,588,402 | 5/1986 | Igari et al. | 604/905 |
| 4,617,012 | 10/1986 | Vaillancourt | 604/905 |
| 4,629,455 | 12/1986 | Kanno | 604/283 |
| 4,642,091 | 2/1987 | Richmond | 604/905 |
| 4,650,475 | 3/1987 | Smith et al. | 604/905 |

OTHER PUBLICATIONS

Stainless Steel Pass—Through Tube, for a Seachrist Monoplace Hyperbaric Chamber.

*Primary Examiner*—C. Fred Rosenbaum
*Assistant Examiner*—Denise Whelton

[57] ABSTRACT

A pass-through tube for use in conveying intravenous fluid to a patient in a pressurized chamber, the tube including a tubular body having an outer surface shaped and sized to sealably mate with the interior surface of a connector passing through the wall of a pressurized chamber, a first end having a first generally cylindrical surface adapted to sealably engage a similarly shaped surface of a mating first connector and first locking members for locking with mating locking members on the first connector, a second end having a second generally cylindrical surface adapted to sealably engage a similarly shaped surface of a mating second connector and second locking members for locking with mating locking members on the second connector. Also disclosed is a kit including a pass-through tube, a flexible internal tube, and a valve connected to the external end for connection to an intravenous supply line.

3 Claims, 1 Drawing Sheet

PASS-THROUGH TUBE FOR PRESURIZED CHAMBER

FIELD OF THE INVENTION

The invention relates to delivering intravenous fluids to patients in pressurized chambers.

BACKGROUND OF THE INVENTION

Patients placed in pressurized chambers (e.g., a Seachrist Monoplace hyperbaric chamber) for treatment of various conditions (e.g., embolism and carbon monoxide poisoning) have been provided with intravenous fluids from bags outside of the chambers by disposable flexible delivery tubes that are connected to both ends of stainless steel pass-through tubes having outer surfaces that sealably fit in connectors defining holes through chamber doors. Between uses with different patients, a pass-through tube must be removed, sterilized and reinstalled in the door with fresh delivery tubes, which slip on and frictionally engage male or female portions of the pass-through tubes.

SUMMARY OF THE INVENTION

In general, the invention features in one aspect improving a pass-through tube for use in delivering intravenous fluid to a patient in a pressurized chamber by providing its connecting ends with locking members for locking with mating locking members on the internal and external connecting members. The locking connections prevent disconnection of the internal tube, for example by movement of the patient in the chamber, or of the external tube, owing to the pressure applied to the intravenous liquid. A disconnection of the internal or external line could result in removal of blood from the patient. A disconnection inside the chamber would require decompression, taking, for example, about 15 minutes, before opening the chamber and reconnecting the delivery line to the patent, to avoid potential patient injury (for example gas expansion in lungs).

In preferred embodiments there are helical locking projections; and the pass-through member has male and female ends; the male end has a rotatable locking member carrying helical threads on it; the pass-through tube is made of plastic and has fins in portion adjacent to a cylindrical sealing portion and a flange for positioning the sealing portion in the connector.

In another aspect the invention features a kit that is for delivering intravenous fluid to a patient in a pressurized chamber and includes a disposable flexible internal delivery tube for connection to a catheter at one end, a disposable plastic pass-through tube connected to the other end of the internal delivery tube and having an outer surface shaped and sized to sealably mate with the interior surface of a connector on the pressurized chamber door, and a valve that is connected to the external end of the disposable pass-through tube and has an accessible end for connection to an intravenous supply.

In preferred embodiments the kit also includes a back check valve connected to the disposable pass-through tube to prevent fluid flow from the interior to the exterior; the pass-through tube is made of clear plastic to permit detection of trapped air in the device during fluid fill; and the valve has two ports to permit access for adding medication.

Other advantages and features of the invention will be apparent from the following description of a preferred embodiment thereof and from the claims.

DESCRIPTION OF THE PREFERRED EMBODIMENT

The preferred embodiment will now be described.

DRAWINGS

STRUCTURE

Figures 1, 2, 3, 4, 5, 6:
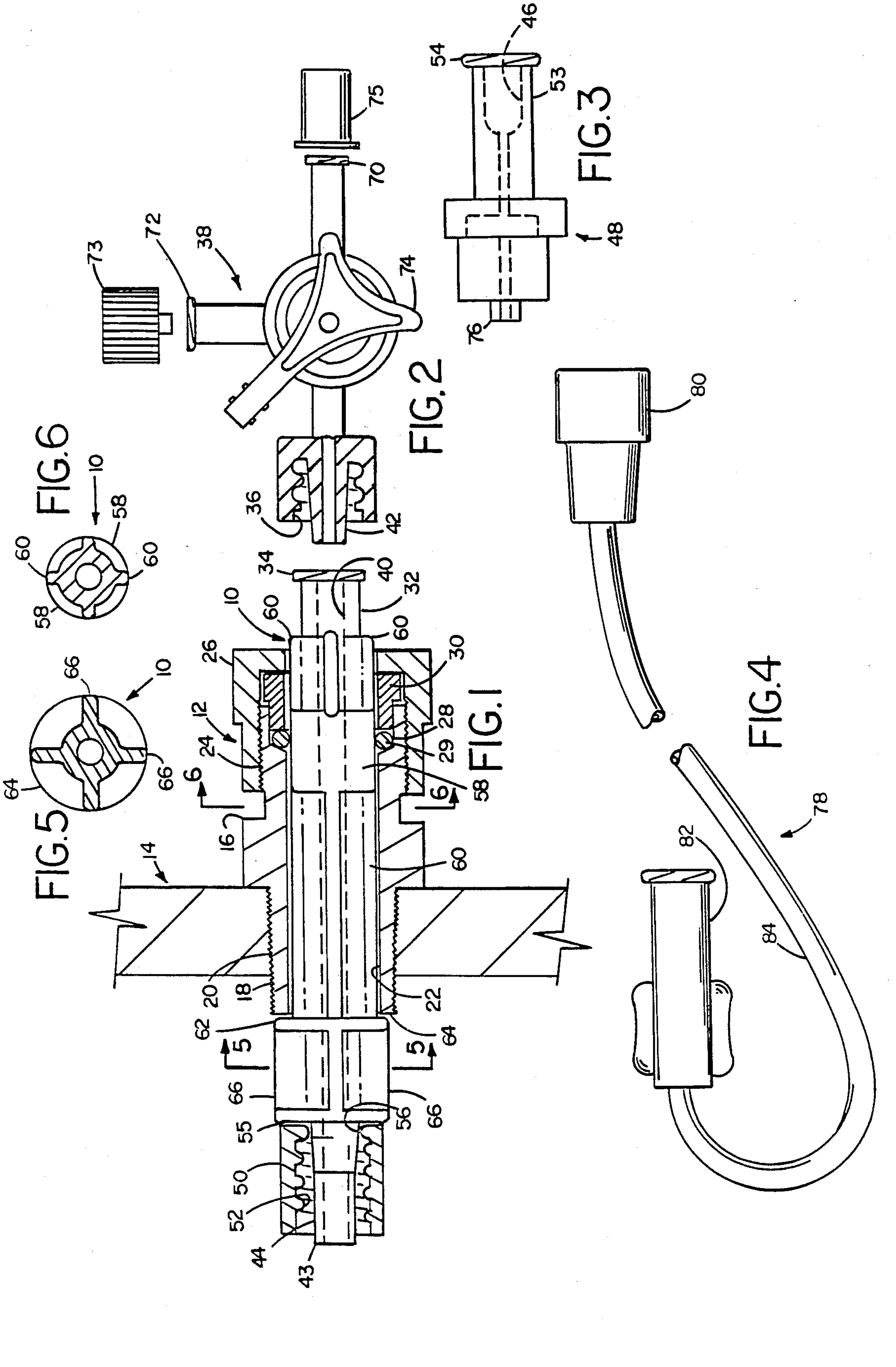
FIG. 1 is a partial sectional view showing a disposable pass-through tube according to the invention mounted in a connector passing through a door of a pressurized chamber.
FIG. 2 is a plan view, partially broken away, of a stop cock valve, for connection to an external female connecting end of the FIG. 1 pass-through tube.
FIG. 3 is a plan view of a back check valve for connection to an internal male connecting end of the FIG. 1 pass-through tube.
FIG. 4 is a plan view of a disposable internal flexible delivery tube for connection between the FIG. 3 back check valve and a catheter.
FIG. 5 is a sectional view, taken at 5—5 of FIG. 1, of the FIG. 1 pass-through tube.
FIG. 6 is a sectional view, taken at 6—6 of FIG. 1, of the FIG. 1 pass-through tube.

Referring to the figures, in FIG. 1 there is shown disposable plastic pass-through tube 10, sealably connected to connector 12, which passes through and is threadedly and sealably connected to door 14 of a pressurized chamber (e.g., a Seachrist Monoplace hyperbaric chamber). Connector 12 (a Cajon Ultra-Torr male connector, 6-UT-1-4) includes tube 16 connected at its threaded end 18 to threads 20 door 14, internal cylindrical passage 22 (0.381" diameter) and threaded external end 24. Connector 12 also includes tightening nut 26, elastomeric O-ring 28 (number 012, 0.070+0.003" diameter), and internal ring 30, positioned to compress O-ring 28 against conical surface 29 when nut 26 is tightened.

Pass-through tube 10 is made of clear polycarbonate and has external female connecting end 32 with helical threads 34, for mating with threads 36 of stop cock valve 38, and internal generally cylindrical (there is a small taper) passage 40 for mating with the similarly shaped outer surface of mating male member 42 of stop cock valve 38. This type of connection is often referred to as a luer lock connection.

On the other side of door 14, pass-through tube 10 has interior male connecting end 43, having generally cylindrical external (slightly expanding) surface 44 for mating with similarly shaped internal surface 46 of back check valve 48. Surrounding male connector end 43 is locking nut 50 having threads 52 for mating with threads 54 of female connecting end 53 of back check value 48, to provide a luer locking connection with it. Locking nut 50 has lip 55, which fits in annular recess 56 of male internal connecting end 43.

Near external female end 32 of pass-through tube 10 is cylindrical sealing portion 58 (0.370" diameter), which is sealably engaged by O-ring 28. On both sides of cylindrical portion 58, tube 10 has fins 60 (FIG. 6). Near internal male member 42 are flange 62, for butting up against end 64 of connector 12, and fins 66 (FIG. 5). Fins 60, 66 are provided to limit volume of plastic to avoid distortions during molding.

Referring to FIG. 2, stop cock valve 38 includes luer-type locking female connectors 70, 72, for connection to an intravenous line and for providing access, respectively. Stop cock valve 38 also includes handle 74 for controlling a closure member (not shown) to selectively connect the flow passage through male member 42 to either connector 70, 72 or to block flow to male member 42. Female luer lock plug 73 is used to stop up connector 72, and sterile cap 75, which is removed prior to use, covers connector 70.

Referring to FIG. 3, back check valve 48 includes within it a one-way flow control member (not shown) that only permits flow in the direction from its female connecting end 53 to male end 76 (tested up to 70 PSI). Referring to FIG. 4, there is shown internal disposable flexible delivery tube 78 having female luer lock connecting end 80, for connection to a catheter, female luer lock connecting end 82, for connection to male end 76 of back check valve 48, and 6 foot long PVC tube 84 therebetween.

Disposable pass-through tube 10 is packaged in a kit with stop cock valve 38, back check valve 48, and disposable flexible tube 78. All four components are connected together in the kit.

OPERATION

Disposable pass-through tube 10 and the other components shown in the drawings are used to provide intravenous (IV) fluid to a patient being treated in a pressurized chamber including door 14. The interior of the chamber, to the left of door 14, is pressurized in use (for example 3 atmospheres), and the right side of door 14 remains at atmospheric pressure. As is explained in more detail below, the kit provides the operator with a disposable, preassembled sterile set which offers ease of setup and increased patient safety.

Prior to use with a new patient, the sterile package containing pass-through tube 10, stop cock valve 38, back check valve 48, and flexible tube 78 is opened, and stop cock valve 38 is removed from tube 10 by rotating to disconnect the luer lock connection. Female end 32 is inserted through passage 22 of connector 12 unit flange 62 butts up against end 64 of connector 12. Locking nut 26 is tightened, axially biasing ring 30 and compressing O-ring 28, which expands in a radial direction and makes a sealable connection between cylindrical surface 58 and conical surface 29 of tube 16. Stop cock valve 38 is then connected to female end 32, male member 42 of stop cock valve 38 sealably engaging inner surface 40 of end 32 and being lockably connected thereto via mating helical threads 34, 36.

An IV bag (not shown) is then connected by its delivery line and an IV pump (both not shown) to luer connection 70 of stop cock valve 38. The pump is activated to fill the line with intravenous fluid, an the operator can verify that there are no trapped bubbles in tube 10, owing to its clear plastic construction. The catheter connected to end 80 of internal delivery tube 78 is inserted into the patient. Door 14 is closed, and the chamber is pressurized.

During pressure treatment of a patient, it might be necessary to replace an intravenous fluid bag after it has emptied. Before this is done, stop cock valve 38 is switched to its closed position; it is then opened after a fresh bag has been connected. Stopcock valve 38 is also used if there is a failure of the external IV lines. Stop cock valve 38 also allows the operator to shut off the fluid supply to the patient during treatment. In the event of accidental disconnection outside of the chamber, back check valve 48 prevents the intravenous fluid from being discharged outward through it. The locking connection between female end 32 of pass-through tube 10 and stopcock valve 38 prevents disconnection during treatment, something which otherwise might be a problem, owing to the 35 PSI pressure in the line. The locking connections between the components inside the chamber prevents accidental disconnection caused by movement of the patient. Connector 72 provides external access to the IV fluid line for the introduction of various medications and female luer lock plug 73 permits one to maintain a sterile site.

After use with a patient, the tube and other members are simply discarded, and there is no need to worry about damage to the parts during handling between treatments.

OTHER EMBODIMENTS

Other embodiments of the invention are within the scope of the following claims. For example, in addition to helical threads, other locking connections can be used, for example, bayonet-type connections.

What is claimed is:

1. The combination comprising a pressure chamber wall carrying a wall connector that passes through it, is sealed thereto and has an interior sealing surface, and a disposable plastic pass-through tube for use in conveying intravenous fluid to a patient in said pressurized chamber, said tube comprising an elongated tubular body having an outer sealing surface shaped and sized to sealably mate with said interior sealing surface of said connector passing through said wall of said pressurized chamber, said body having an axial flow passage through it, said outer sealing surface having a cylindrical surface over a sealing portion of said tube, axial fins along another portion of said tube, a first end having a first generally cylindrical surface adapted to sealably engage a similarly shaped surface of a mating first connector and first locking members for locking with mating locking members on said first connector, and a second end having a second generally cylindrical surface adapted to sealably engage a similarly shaped surface of a mating second connector and second locking members for locking with mating locking members on said second connector.

2. The combination of claim 1 further comprising a radially extending flange located at a predetermined axial position with respect to said sealing portion so as to position said sealing portion in said connector.

3. A disposable, plastic pass-through tube for use in conveying intravenous fluid to a patient in a pressurized chamber, said tube comprising an elongated tubular body having an outer sealing surface shaped and sized to sealably mate with the interior surface of a connector passing through a wall of pressurized chamber, said body having an axial flow passage through it, said outer sealing surface being a cylindrical sealing surface over a sealing portion of said tube, another portion of said tube having projecting portions extending outward from a smaller diameter than that of said cylindrical surface, a first end having a first generally cylindrical surface adapted to sealably engage a similarly shaped surface of a mating first connector and first locking members for locking with mating locking members on said first connector, and a second end having a second generally cylindrical surface adapted to sealably engage a similarly shaped surface of a mating second connector and second locking members for locking with mating locking members on said second connector.

* * * * *

UNITED STATES PATENT AND TRADEMARK OFFICE
CERTIFICATE OF CORRECTION

PATENT NO. : 4,820,280

DATED : April 11, 1989

INVENTOR(S) : Berch et al.

It is certified that error appears in the above-identified patent and that said Letters Patent is hereby corrected as shown below:

In the Title, "PRESURIZED" should be --PRESSURIZED--;

Column 1, line 1, "PRESURIZED" should be --PRESSURIZED--;

Column 1, line 47, "portion" should be --portions--;

Column 2, line 36, after "20" insert --in--;

Column 2, line 39, "+" should be --±--;

Column 3, line 42, "unit" should be --until--;

Column 3, line 55, "an" should be --and--;

Column 4, line 60, before "pressurized" insert --a--.

Signed and Sealed this

Twenty-fifth Day of December, 1990

*Attest:*

HARRY F. MANBECK, JR.

*Attesting Officer* *Commissioner of Patents and Trademarks*